United States Patent [19]

Ohtsuka et al.

[11] Patent Number: 5,430,050
[45] Date of Patent: Jul. 4, 1995

[54] HISPIDOSPERMIDIN

[75] Inventors: Tatsuo Ohtsuka, Kamakura; Akiko Sakai, Yokohama; Toru Okuda, Fujisawa, all of Japan

[73] Assignee: Hoffmann-La Roche Inc., Nutley, N.J.

[21] Appl. No.: 156,143

[22] Filed: Nov. 22, 1993

[30] Foreign Application Priority Data

Dec. 4, 1992 [EP] European Pat. Off. ............ 92120686

[51] Int. Cl.⁶ .................... A61K 31/34; C07D 307/00
[52] U.S. Cl. .................... 514/410; 549/354; 435/41; 435/53
[58] Field of Search ............ 514/410; 549/354

[56] References Cited

FOREIGN PATENT DOCUMENTS 349224 6/1989 European Pat. Off. ............ 544/296

OTHER PUBLICATIONS

Nordlander, J. E., et al., Journal of Organic Chemistry, vol. 49, No. 1, pp. 133–138 (1984).

Sechi, A. M., et al., Archives of Biochemistry and Biophysics, vol. 186, No. 2, pp. 248–254, Mar. 1978.

*Primary Examiner*—Alan L. Rotman
*Attorney, Agent, or Firm*—George M. Gould; William H. Epstein; Raina Semionow

[57] ABSTRACT

The compound of formula,

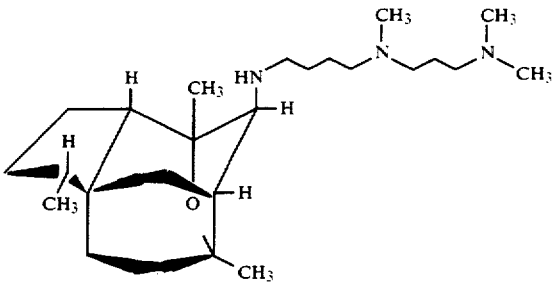

is obtained from cultures of *Chaetosphaeronema hispidulum*. The compound is an inhibitor of phospholipase C.

6 Claims, No Drawings

HISPIDOSPERMIDIN

The present invention relates to a novel compound having the formula I,

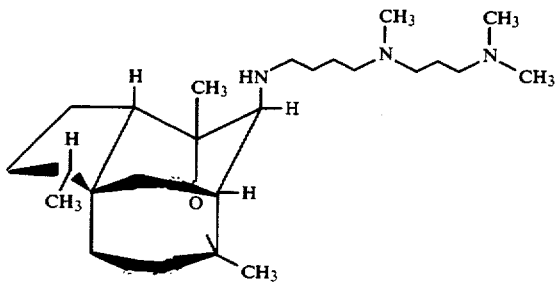

the compound also known as hispidospermidin, and pharmaceutically acceptable salts thereof.

The present invention also relates to a pharmaceutical composition containing hispidospermidin as a phospholipase C (PLC) inhibiting composition, and a process for making hispidospermidin.

It is well known that inositolphosphates and their degraded products play an important role in the signal transduction for cell growth and transformation. One of these signaling pathways is proceeded by activation of PLC. The binding of first messengers such as mitogens, hormones, growth factors, neurotransmitters to their specific cellular receptors, activates the enzyme, PLC. Activated PLC cleaves phosphatidylinositol 4,5-diphosphate ($PIP_2$) (phosphatidylinositol referred to herein as "PI") into 2 kinds of second messengers, namely diacylglycerol (DG) and inositol triphosphate ($IP_3$). DG activates protein kinase C (PKC) and $IP_3$ increases intracellular $Ca^{++}$ level. These two second messengers trigger various physiological responses of cells through different pathways.

Thus, PLC is one of the effective targets to block deregulated proliferative and/or inflammatory signals and thus, PLC inhibiting activity is predictive of anti-tumor and/or anti-inflammatory activity.

In accordance with the present invention, it has been found that hispidospermidin has potent PLC inhibiting activity.

The physico-chemical properties of hispidospermidin as described in the Example hereinbelow is as follows:

| | |
|---|---|
| Appearance: | Colorless oil |
| $[\alpha]_D^{24}$ | $-60°$ (c 1.45, $CHCl_3$) |
| Molecular formula: | $C_{25}H_{47}N_3O$ |
| *HREI-MS (m/z) $M^+$: | Calcd. for $C_{25}H_{47}N_3O$:405.3720 Found.: 405.3730 |
| $UV\lambda_{max}^{MeOH}$ nm: | End absorption |
| $IR\nu_{max}$ (neat) $cm^{-1}$: | 3600~3100, 2780, 2760 |
| Solubility: | Soluble in MeOH, $CHCl_3$, acetone, acidic water Insoluble in water |
| $^1H$ NMR (400 $MH_z$, $CDCl_3$) d: (TMS was used as an internal standard.) | 0.82 (3H, d, J = 7 Hz), 1.12 (3H, s), 1.13(1H, m), 1.22 (3H, s), 1.22 (1H, dd, J = 8, 13 Hz), 1.28 (1H, d, J = 12.5 Hz), 1.40 (1H), 1.42 (1H, m), 1.45 (1H, dd, J = 5, 12.5 Hz), 1.48 (1H), 1.50 (2H, m), 1.51 (2H, m), 1.52 (1H, m), 1.57 (1H, m), 1.64 (2H, m), 1.71 (1H, m), 1.73 (1H, m), 1.77 (1H, dd, J = 7.5 13 Hz), 2.03 (1H, t, J = 5 Hz), 2.22 (9H, s), 2.28 (2H, br t, J = 7Hz), 2.34 (2H), 2.35 (2H), 2.60 (2H, t, J = 7Hz), 2.81 (1H, d, J = 5 Hz) |
| $^{13}C$ NMR (100 $MH_z$, $CDCl_3$) d: (TMS was used as an internal standard.) | 14.1, 18.1, 20.3, 21.0, 25.1, 25.6, 27.3, 28.6, 28.9, 29.4, 32.2, 42.3, 43.2, 43.4, 44.5, 45.6, 48.6, 51.9, 55.9, 57.8, 58.0, 66.4, 80.0, 81.7 |

*HREI-MS: High resolution electron impact mass spectrometry.

According to the process provided by the present invention, hispidospermidin is produced by cultivating a microorganism belonging to the genus Chaetosphaeronema capable of producing hispidospermidin under aerobic condition in an aqueous culture medium and isolating hispidospermidin from the culture.

The microorganism used in the foregoing process can be any strain (including variants) belonging to the genus Chaetosphaeronema capable of producing hispidospermidin. Especially preferred strains are Chaetosphaeronema hispidulum NR7127 as well as variants thereof. Chaetosphaeronema hispidulum NR7127 was isolated from a soil sample and identified as a strain belonging to the genus Chaetosphaeronema.

The strain denoted as Chaetosphaeronema hispidulum NR7127 has been deposited with the Fermentation Research Institute, Agency of Industrial Science and Technology, Japan, under the Budapest Treaty on Nov. 25, 1992 as follows: Chaetosphaeronema hispidulum (CdA) Moesz NR 7127 (FERM BP-4081)

The culture characteristics and the morphological characteristics of Chaetosphaeronema hispidulum NR7127 (FERM-BP 4081 ) are as follows:

CULTURAL CHARACTERISTICS

Dark brown to black colonies grew on malt extract agar showing floccose appearance. Exudates or soluble pigments were not produced. No conidiogenesis was observed under normal fluorescent or natural light. Under near UV light, however, numerous conidiomata half submerged in agar were formed after several weeks. Cultivation on banana leaf agar was the most effective for conidiomata production.

MORPHOLOGICAL CHARACTERISTICS

The conidiomata were pycnidial, dark brown to black, globose to subglobose, and up to 450 μm in diam. Ostioles were single, central and slightly beaked. Numerous bristly setae were restricted around the beak and were septate and straight. The conidiogenous cells with collarette were phialidic, cylindrical and hyaline, 6.0–10.5×3.0–7.5 μm, and their periclinal walls were thick. The conidia were hyaline, one-septate, smooth, straight to slightly curved, and their apex and base were obtuse. Their size was 11.5–16.0×1.5–3.5 μm.

The conidiomata had numerous setae. The conidiogenous cells were phialidic. The conidia were one-septate, hyaline and straight to curved. There characteristics clearly indicated that this strain was included in the genus Chaetosphaeronema Moesz (Sutton, 1980). Further properties such as the sizes of conidiomata, conidiogenous cells and conidia indicated that this strain should be Chaetosphaeronema hispidulum Moesz. The beaks of this strain were not as long as those of the herbarium specimen, *Chaetosphaeronema hispidulum* IMI 182342. In a personal communication with Dr. Sutton (International Mycological Institute,Kew, England), it was suggested that the difference can be neglected. Therefore this strain was identified as *Chaetosphaeronema hispidulum* Moesz.

The cultivation in accordance with the process provided by the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are, for example, soybean meal, cottonseed meal, meat extract, peptone, dried yeast, yeast extract, cornsteep liquor, ammonium sulfate, sodium nitrate and mixtures thereof. Moreover, there may be added to the culture medium other organic or inorganic substances for promoting the growth of the microorganism and for increasing the production of hispidospermidin, examples of such substances being inorganic salts such as, for example, calcium carbonate, sodium chloride, phosphates and the like.

The cultivation is carried out under aerobic conditions in an aqueous medium, preferably by submerged fermentation. The cultivation is suitably carried out at a temperature of 20° C.–35° C., the optimal temperature being 27° C. The cultivation is preferably carried out at a pH of 3 to 9. The cultivation time depends on the conditions under which the cultivation is carried out. In general, it is sufficient to carry out the cultivation for 50~200 hours.

The isolation of hispidospermidin from the fermentation broth can be carried out according to methods known to those skilled in the art. For example, the mycelium can be separated from the fermentation broth by centrifugation or filtration and hispidospermidin can be extracted from the filtrate with a water-immiscible organic solvent such as alkanol e.g. n-butanol and esters e.g. ethyl acetate, butyl acetate etc. On the other hand, hispidospermidin contained in the separated mycelium can be obtained, for example, by extracting the mycelium with a solvent such as aqueous acetone or aqueous methanol, removing the solvent and further extracting the residue with a water-immiscible organic solvent. The thus-obtained solvent layer is dried over a dehydrating agent such as sodium sulfate etc. and then concentrated under reduced pressure. The resulting crude hispidospermidin can be purified by means of extraction methods, partition methods, precipitation methods, column-chromatographical methods (using silica gel, aluminum oxide, Diaion HP-21, ion exchange resin etc. as adsorbents).

Inhibitory activity of hispidospermidin against PLC was measured.

The assay mixture (0.1 ml) contained 200 mM Tris-acetate buffer (pH 5.5), 2 mM $CaCl_2$, 250 μM PI (suspended in the buffer, specific activity: 800 dpm/nmole) and enzyme.

In the standard assay, 20 μl of inhibitor in 15 mM Tis-HCl buffer (pH 7.5) was added to the substrate suspension (50 μl). The reaction was started with addition of the enzyme solution prepared from partially purified rat brain PLC (30 μl, ca. 5 μg protein) and incubated for 20 min. at 30° C. The reaction was terminated by adding 0.3 ml of unlabeled PI (200 μM) solution containing 1 mg/ml of bovine serum albumin and 1 mM EGTA, followed by adding of 0.3 ml of 7.5% ice cold trichloroacetic acid containing 3 mM $CaCl_2$. Under the conditions, the enzyme hydrolyzed about 30% of substrate in the assay mixture. As a positive control showing 100% inhibition of PLC, 20 μl of 25 mM EDTA was added to the assay mixture.

The incubation mixture was kept on ice for 10 min and centrifuged at 1,700×g for 10 min. The radioactivity of an aliquot (0.2 ml) of the supernatant was measured by liquid scintillation counter (ALOKA).

Inhibitory activity of hispidospermidin against PLC is shown in Table I.

TABLE I

| Compounds | $IC_{50}$ (μM) |
|---|---|
| Hispidospermidin | 15.7 |
| Quinacrine | 314.4 |
| Tobramycin | 29.9 |
| Sperimine | 59.3 |
| Trifluoperazine | 149.7 |

Acute toxicity of hispidospermidin is not observed.

The novel hispidospermidin provided by the present invention can find use as medicaments particularly in the treatment of inflammatory diseases, such as psoriasis, inflammatory bowel disease, asthma, allergy, arthritis, dermatitis, gout, pulmonary disease, myocardial ischemia, and trauma induced inflammation, such as spinal cord injury. The medicaments can be particularly for the treatment of tumors and/or inflammatory conditions. The medicaments can be for oral or parenteral application, in the form of unit dose pharmaceutical preparations which contain them or their pharmaceutically acceptable salts in admixture with an organic or inorganic therapeutically inert carder material suitable for enteral application, such as for example water, gelatine, gum arabic, lactose, starch, magnesium stearate, talc, vegetable oils, polyalkylene glycols etc. The unit dose pharmaceutical preparations can be present in solid form, e.g. as tablets, coated tablets, dragees or capsules, hard gelatine or sort gelatine, or in liquid form, e.g. as solutions, syrups, or suspensions.

The compound of formula I and its pharmaceutically acceptable salts can be used also for parenteral administration, and for this purpose, are preferably made into preparations as lyophilisates or dry powder for dilution with customary agents, such as water or isotonic common salt solutions.

A dose unit may contain 10 to 200 mg of active ingredient. The daily dosage for an adult can be in the range from 10 to 400 mg and may be varied according to individual requirements which can be determined by those of ordinary skill in the art.

The following example further illustrates the present invention.

EXAMPLE

A portion of the stock culture (0.1 ml) of *Chaetosphaeronema hispidulum* NR7127 (FERM-BP No. 4081) was inoculated into a 500 ml flask containing 100 ml of a medium consisting of 2% glucose, 2% potato starch, 2% Toast soya, 0.5% yeast extract, 0.25% NaCl, 0.005% $ZnSO_4 \cdot 7H_2O$, 0.0005% $CuSO_4 \cdot 5H_2O$, 0.0005% $MnSO_4 \cdot 4H_2O$, 0.32% $CaCO_3$ and 0.03% Nissan disfoam CA-115. The pH of the medium was adjusted to 7.0 before the addition of calcium carbonate. This seed culture was shaken on a rotary shaker at 190 rpm at 27° C. for 4 days. Two ml of the resultant culture was transferred into each of six 500 ml flasks containing the same medium and cultured under the same conditions for 3 more days. Six hundred milliliters of the second seed culture was inoculated into a 50-liter jar fermentor containing 30 liters of the same medium and 0.3% disfoam. The fermentation was conducted at 27° C. at an aeration rate of 30 liters/min and agitated at 500 rpm for 95 hours. The maximum yield of hispidospermidin was reached at around 70 hours of fermentation.

The harvested broth filtrate (17 liters) was adjusted to pH 7 with 1N HCl and applied to a column of Amberlite IRC-50 (Na/H=7/3) (Rohm and Haas). The column was washed with water and then the active principle was eluted with 0.5N HCl. The eluate was adjusted to pH 7 with 3N NaOH and applied to a column of Diaion HP-21 (Mitsubishi Chemical Industries is Ltd.). The active principle was eluted with water and successively 10% aqueous acetone. Combined active fractions were concentrated to remove acetone and extracted ethyl acetate at pH 9. The organic layer was evaporated under reduced pressure to give hispidospermidin (2.6 g) as a colorless oil.

The following example illustrates a pharmaceutical preparation containing hispidospermidin provided by the present invention:

EXAMPLE

Tablets each containing the following ingredients were manufactured in the conventional manner per se:

| | |
|---|---|
| Hispidospermidin | 100 mg |
| Starch | 26 mg |
| Carboxymethylcellulose calcium | 15 mg |
| Crystalline cellulose | 20 mg |
| Magnesium stearate | 4 mg |
| | 165 mg |

We claim:

1. A compound of formula I,

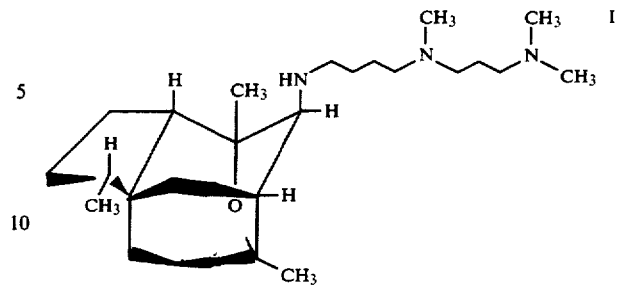

or a pharmaceutically acceptable salt thereof.

2. A pharmaceutical composition comprising a therapeutically effective amount of a compound of formula I,

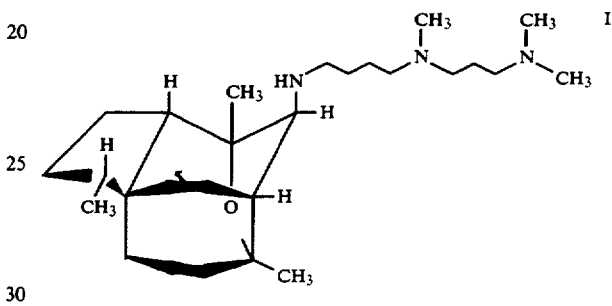

or a pharmaceutically acceptable salt thereof, and a therapeutically inert carrier.

3. The composition of claim 2 wherein the amount of said compound of formula I is from about 10 mg to about 200 mg.

4. The composition of claim 2 which is in unit dosage form.

5. The pharmaceutical composition of claim 4 wherein said unit dosage form is selected from a group consisting of tablets, coated tablets, dragees, hard gelatine capsules, soft gelatine capsules, solutions, syrups and suspensions.

6. The pharmaceutical composition of claim 5 wherein the amount of said compound of formula I in the unit dosage form is from about 10 mg to about 200 mg.

* * * * *

UNITED STATES PATENT AND TRADEMARK OFFICE
CERTIFICATE OF CORRECTION

PATENT NO. : 5,430,050
DATED : July 4, 1995
INVENTOR(S) : Tatsuo Ohtsuka, Toru Okuda and Akiko sakai It is certified that error appears in the above-indentified patent and that said Letters Patent is hereby corrected as shown below:

In the title page, under Abstract; in Column 1, line 7; and in Column 6, Claim 1, line 1 and Claim 2, line 20, in each instance, the chemical formula (formula I) should be as follows:

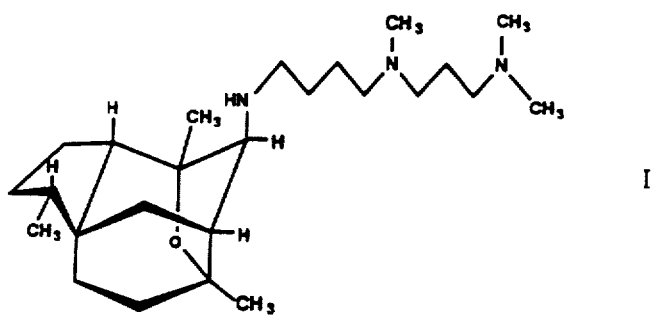

I

Signed and Sealed this

Twenty-first Day of November, 1995

Attest:

BRUCE LEHMAN

Attesting Officer

Commissioner of Patents and Trademarks